(12) United States Patent
Valk et al.

(10) Patent No.: US 11,621,071 B2
(45) Date of Patent: Apr. 4, 2023

(54) SYSTEM AND METHOD FOR CLINICAL QUALITY AND SAFETY AUTOMATION

(71) Applicant: ADMETSYS CORPORATION, Boston, MA (US)

(72) Inventors: Jeffrey Valk, Boston, MA (US); Glenn Robertelli, Boston, MA (US)

(73) Assignee: ADMETSYS CORPORATION, Boston, MA (US)

( * ) Notice: Subject to any disclaimer, the term of this patent is extended or adjusted under 35 U.S.C. 154(b) by 77 days.

(21) Appl. No.: 16/976,100

(22) PCT Filed: Mar. 12, 2019

(86) PCT No.: PCT/US2019/021758
§ 371 (c)(1),
(2) Date: Aug. 27, 2020

(87) PCT Pub. No.: WO2019/178028
PCT Pub. Date: Sep. 19, 2019

(65) Prior Publication Data
US 2021/0043307 A1      Feb. 11, 2021

Related U.S. Application Data

(60) Provisional application No. 62/641,719, filed on Mar. 12, 2018.

(51) Int. Cl.
| | | |
|---|---|---|
| *G16H 40/20* | (2018.01) | |
| *G16H 70/60* | (2018.01) | |
| *G16H 10/60* | (2018.01) | |
| *G16H 50/70* | (2018.01) | |
| *G16H 20/10* | (2018.01) | |

(Continued)

(52) U.S. Cl.
CPC ........... *G16H 40/20* (2018.01); *G06F 21/602* (2013.01); *G06Q 50/28* (2013.01); *G16H 10/60* (2018.01);

(Continued)

(58) Field of Classification Search
CPC ........ G16H 40/20; G16H 10/60; G16H 20/10; G16H 50/70; G16H 70/20; G16H 70/60;
(Continued)

(56) References Cited

U.S. PATENT DOCUMENTS

2005/0267356 A1   12/2005   Ramasubramanian et al.
2006/0125356 A1*   6/2006   Meek .................. A61G 12/001
                                                         312/215
(Continued)

FOREIGN PATENT DOCUMENTS

WO      2011041281 A1      4/2011
WO   WO-2011041281 A1 *    4/2011   ........... G06F 19/322
(Continued)

OTHER PUBLICATIONS

Haefeli et al., "Electronic decision support to promote medication safety", Bundesgesundheitsblatt Gesundheitsforschung Gesundheitsschutz (2018), 61(3)1271-277 (Abstract only).

(Continued)

*Primary Examiner* — Joy Chng
(74) *Attorney, Agent, or Firm* — Fox Rothschild LLP

(57) ABSTRACT

The system and method in accordance with the invention accepts a treatment order from a clinician, which is captured as data. The order data identifies, at a minimum, the patient to be treated, and the treatment to be administered. Additional data may be included. The data is transmitted to one or more fulfillment centers based on supply availability. The supplies are tagged with an information-carrying facet and transported to the patient point of care. At the patient point of care the supplies' data tag, the order date and the patient identity is verified. If verification is correct then the supplies are used to treat the patient. The process may be monitored and/or audited.

20 Claims, 1 Drawing Sheet

(51) Int. Cl.
*G16H 70/20* (2018.01)
*G06F 21/60* (2013.01)
*G06Q 50/28* (2012.01)

(52) U.S. Cl.
CPC ............ *G16H 20/10* (2018.01); *G16H 50/70* (2018.01); *G16H 70/20* (2018.01); *G16H 70/60* (2018.01); *G06Q 2220/00* (2013.01)

(58) Field of Classification Search
CPC .. G06F 21/602; G06Q 50/28; G06Q 2220/00; G06Q 10/06395; G06Q 10/087; G06Q 40/08
USPC ....................................................... 705/2–3
See application file for complete search history.

(56) References Cited

U.S. PATENT DOCUMENTS

| | | | | |
|---|---|---|---|---|
| 2006/0287887 | A1* | 12/2006 | Hutchinson | A61M 5/168 705/2 |
| 2009/0167531 | A1 | 7/2009 | Ferguson | |
| 2012/0303388 | A1* | 11/2012 | Vishnubhatla | G16H 50/20 705/2 |
| 2015/0250948 | A1 | 9/2015 | Gupta et al. | |

FOREIGN PATENT DOCUMENTS

| | | | |
|---|---|---|---|
| WO | 2017027673 A1 | 2/2017 | |
| WO | WO-2017027673 A1 * | 2/2017 | ............ A61J 7/0418 |

OTHER PUBLICATIONS

Bertsche et al., "Patient safety based on computer-assisted drug therapy. Electronic check-up of the patient", Internist (Berl) (2009), 50(6)1748-756 (Abstract only).

International Search Report and Written Opinion dated May 30, 2019, for related PCT application No. PCT/US2019/021758, 12 pages.

* cited by examiner

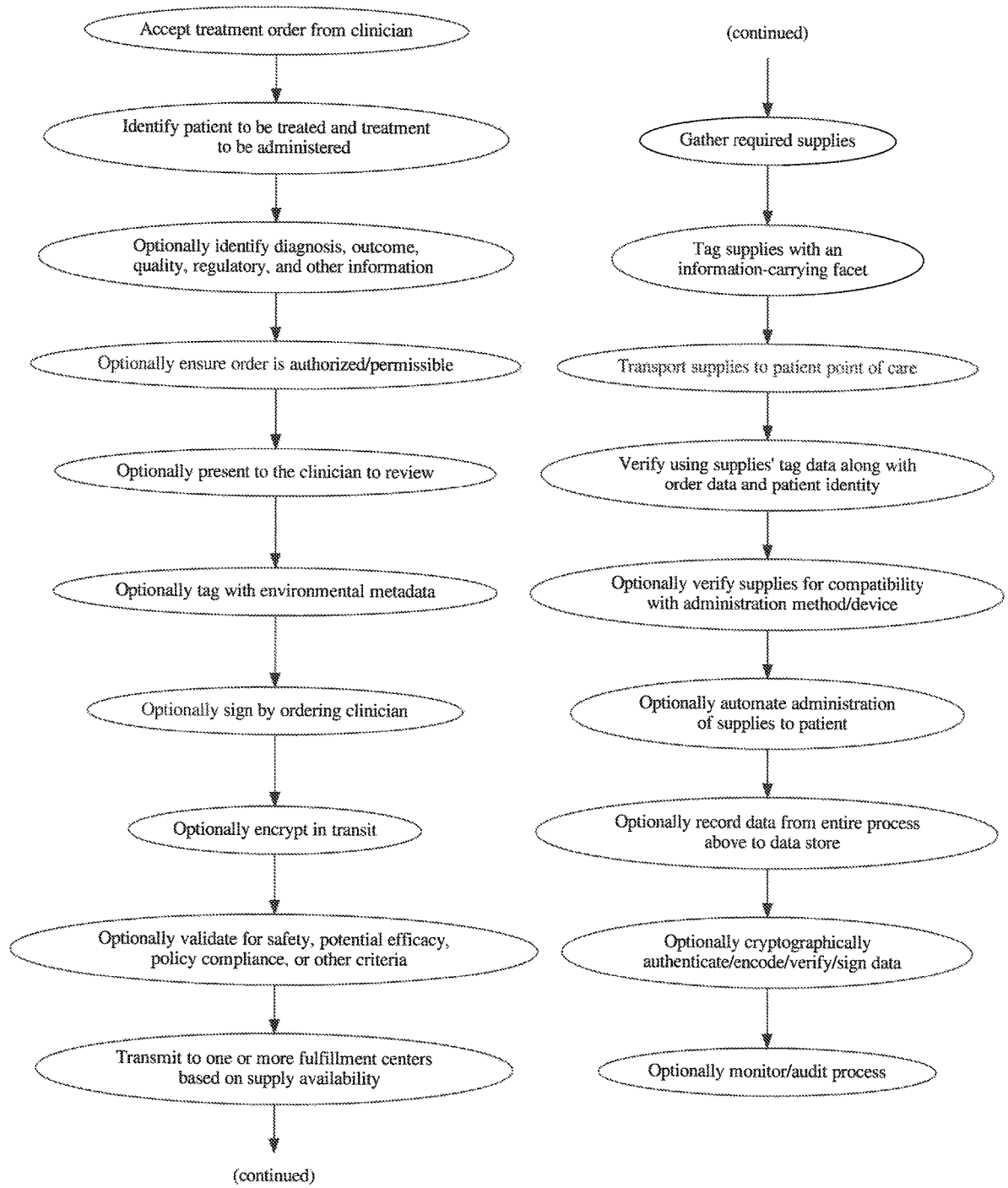

SYSTEM AND METHOD FOR CLINICAL QUALITY AND SAFETY AUTOMATION

FIELD OF THE INVENTION

This invention relates to the delivery of medications within a hospital or clinical setting. More particularly, this invention relates to the quality and safety of the delivery of medications within a hospital or clinical setting.

BACKGROUND OF THE INVENTION

In a hospital or clinical setting, quality and safety of medication delivery is commonly the responsibility of the pharmacist. This assignment is rife with structural challenges. For example, pharmacists have relatively infrequent contact with the patient, and both the initiation and administration of a medication order is out of their direct control. Quality assurance of this life-sustaining function is therefore dependent on reliable information, a proposition which remains highly stressful and challenging for all involved.

Today, medication workflow is similar to the following: A physician prescribes a medication and an associated administration regimen for a patient, often handwritten on paper. The pharmacist interprets this, fills the order, and sends it to the floor. A nurse must then administer the medication to the correct patient, in the correct dosage, with the correct frequency, at the correct time, for the correct duration. Information about what was done, when, and by whom must be recorded by each party; and the pharmacist must certify all steps have been performed as required.

This process is cumbersome, unreliable, and has consequences for patient safety, security, legal liability and exposure, dependability of recordkeeping, clinical efficiency, and cost of care, among others.

What is needed therefor is an integrated set of tools designed to manage medication and associated information flows that includes controls minimize error in the processes involved in the delivery, management, dispensing and administering the medications. The impact of such tools need not be confined to medication-related treatment, though. Similar benefits may be obtained in managing therapies that do not use medication, but have similar workflows. Likewise, such benefits may be obtained for workflows in which supplies or materials are required for other purposes such as diagnostic use, hygiene and sanitation, patient comfort, quality control, maintenance, recordkeeping, compliance.

BRIEF SUMMARY OF THE INVENTION

A system and method for clinical quality and safety is provided. The system and method includes initiating and accepting a treatment order from a clinician through to tracking, dispensing and administration of medications to individual patients in a hospital or clinical setting.

A processing unit includes memory having patient information regarding patients in the hospital or clinical setting including age, allergies to medication, disease state that caused admission, known treatments that are effective in treating the disease state and the like. The processing unit memory also includes information regarding fulfillment centers and availability of supplies and medications by the fulfillment center. This information is updated daily. In addition data including treatment diagnoses, outcome, quality, regulatory and other like data is stored in memory.

A first patient specific treatment order for a first patient and the treatment supplies that fulfills the order is input into the processing unit. The treatment may be a first medication or other type of supply (bandages, saline bags, washes, etc.) Information also input into the order includes dosage (if a medication is included in the order), administration including frequency, timing, and the like. The patient to be treated and the treatment to be administered is verified by the processing unit, i.e. that the patient appears in the hospital admission records and is currently a patient at the hospital and other like criteria as may be appreciated by those of skill in the art. The processing unit communicates the first patient specific medication order through one or more networks to an order management system operated by the fulfillment center that is integrated with the processing unit or which may be located remote from the processing unit, the order management system accessible through the one or more networks. The delivery of the information to an appropriate fulfillment center is based on the availability at the fulfillment center of the particular supplies and medications ordered. The required supplies are requisitioned through the order management system and an updated count of supplies and medications at the particular fulfillment center is update in the processing unit. The ordered supplies and medications to be administered are tagged with an information-carrying facet containing appropriate patient and administration information. The ordered supplies that fulfill the ordered treatment are transported to the patient point of care. The tag is scanned into a computing mechanism that communicates via one or more networks with the processing unit and the information is again verified. Optionally the ordered supplies are cross-referenced by the processing unit with the disease state data stored in memory and verified by the processing unit for compatibility in treating the identified patient disease state.

Administration of supplies including medications may be automated and verified by the processing unit. An electronic administration record associated with the first medication and the first treatment order for the first patient is created and accessible through the one or more networks, and includes information regarding: (i) dispensing actions of the first medication including the administration schedule of the first medication for the first patient; storing the at least the first electronic record associated with the first medication for the first patient in the processing unit. The electronic record is updated as the treatment schedule evolves.

Those of skill in the art will appreciate that the processing unit is configured to process information and treatments orders related to multiple patients.

These and outer features of the invention will now be described below.

BRIEF DESCRIPTION OF THE DRAWINGS

For a better understanding of the invention, and to show how the same may be carried into effect, reference will now be made, by way of example, to the accompanying drawings, in which:

FIG. 1 is a flow diagram illustrating the system and method of clinical quality and safety in accordance with the invention.

DETAILED DESCRIPTION OF THE INVENTION

Referring now to FIG. 1, the system and method in accordance with the invention accepts a treatment order from a clinician, which is captured as data. This capture may be electronic using a traditional desktop or laptop computer, a mobile or wearable device, handwriting or glyph recognition, an environmental interface such as voice recognition or gesture control, a pervasive computing or augmented reality system, or any other type of interface yielding data capable of being processed in the manner described below.

The order data identifies, at a minimum, the patient to be treated, and the treatment to be administered. Additional data may include rationale for the treatment, the expected or desired outcome of the treatment, additional clinician notes, and/or any other information useful to the clinical process or required by regulation or protocol. The order may optionally be checked to ensure the clinician is authorized to issue it for the patient to be treated. The order data may also optionally be presented to the clinician to verify that the information captured is as the clinician intended.

The order data may be optionally tagged with additional metadata such as time and place of the order, whether it was given remotely or at the point of care, pointers to relevant information handled by the described system or other external systems, and/or other information available to the described system at the time of the order. In addition, the order data may be optionally tagged to uniquely and verifiably identify the ordering clinician, using techniques, in isolation or combination, including but not limited to authentication against a trusted system, biometrics, secure tokens, and/or cryptographic signing. The order data may optionally be secured in transit using transport encryption.

The order data may optionally be validated for safety, potential efficacy, policy compliance, or other criteria. Such validation may be by one or more additional persons trained in this discipline, and/or by one or more computer systems, including those leveraging machine learning, expert systems, or other suitable approaches. The order data is transmitted to one or more fulfillment centers, with routing based on the supplies required to execute the order. In the instance that the order calls for medication, fulfillment may come from the pharmacy. In the instance that the order calls for medical device(s), it may cone from central supply. These fulfillment centers may be on premise or remote.

Capability is available at the fulfilment center to fill the order. This may include human fulfilment personnel, such as pharmacists or supply specialists, and may also include robotics and other fulfilment automation. The supplies required for the order are tagged with an information-carrying facet. This identification may occur either during fulfilment or at a previous point in the supply chain, such as during original manufacture, upstream provisioning, or retail sale. This facet may be a simple passive component such as a barcode, QR code, NFC tag, RFID tag, or the like; or may contain active components such as processing electronics and on-board storage; or may have any other embodiment capable of communicating information. The information conveyed by this component may be a simple ID, a reference to external information or systems, a full database of attributes and their history, and/or any other type of information.

The supplies are transported to the patient point of care. This may optionally be by a robotic mechanism or autonomous transport vehicle. Information pertaining to transport may optionally be captured, including transport mode, specific vehicle or apparatus, operator, route, time, distance, environmental data such as temperature humidity, and other information.

The supplies are verified at the patient point of care by examining the information on the supplies' tag(s), with the order data and the identity of the patient to be treated. The supplies are also optionally verified for compatibility with a specific method or device for introduction or administration to the patient. This may include verifying that a delivery device has sufficient precision, accuracy, and safeguards to deliver a medication of a given concentration. The supplies may also be optionally introduced or administered to the patient automatically according to the order data, such as by robotic means.

Data from the entire process may be optionally recorded to a data store. This data store may a centralized database, distributed ledger or distributed database, or any other type of repository for information. Data from all or part of the process may optionally be verified cryptographically, such as through block chain technology.

The system and method in accordance with the invention is optionally monitored and/or audited either periodically or in real time, including by personnel with relevant expertise, and/or computer systems suitable to this task including those leveraging various artificial intelligence techniques.

In one aspect of the invention, the system captures a clinician's order to administer intravenous pharmaceutical medications to a patient. The order is captured via the user interface of a computing device, recorded in a data store, and then made available to the hospital pharmacy. At the pharmacy, an electronic memory chip is provisioned for the medication. The pharmacist fills the order, and attaches the chip to the medication container. Alternatively, the pharmacist may select medication in container to which a chip has been attached in advance. The system relates the specific container to the specific treatment order. This binds the medication container to information about its contents including medication, concentration, source, fill date, expiry date, and other information about the medication; and links the specific medication container directly to the original clinician's order.

The chipped medication container is now sent to the patient point of care, where it is inserted into an intelligent infusion pump. This pump-container combination may be as described in U.S. Pat. No. 9,242,039 ("System and Method for Differentiating Containers in Medication Delivery"), the entirety of which is hereby incorporated by reference. The method for verifying the compatibility of a fluid container with a fluid delivery device for delivery of a medication in accordance with a treatment plan includes providing a fluid container having a chamber structured to hold said medication therein, the fluid container including a geometric mating member extending from an outer surface thereof and a data fixture on said geometric mating member or container for sensing and transmitting information regarding one or more properties of said geometric mating member or said container both; providing a delivery device operable to deliver said medication from the chamber of the fluid container, the delivery device including a geometric mating receptacle structured to physically mate with said geometric mating member, and communicate with said data fixture regarding said one or more properties of said geometric mating member, said container or both; providing sensing means positioned on said delivery device and operable for sensing and transmitting information about said container; verifying physical compatibility between the fluid container and the delivery device by mating at least a portion of the geometric mating member of the fluid container with the geometric mating receptacle of the delivery device; providing a controller in communication with said sensing means and said data fixture and operable to process information transmitted by said sensing means and said data fixture, said controller having stored information regarding a physiological condition of a patient and the treatment plan; accepting or rejecting said information transmitted by said sensing means and said data fixture regarding said one or more properties of said geometric mating member, said container or both; if said information transmitted by said sensing means or said data fixture regarding said one or more properties of said geometric mating member or said container, or both may be accepted by said controller then accepting or rejecting said information about said medication and determining whether said medication is compatible with said treatment plan; and if said medication is compatible with said treatment plan causing said delivery device to deliver said medication to a patient according to said treatment plan.

The infusion pump is programmed with identification of the patient being treated, and connected to the referenced data store, giving it access to the original clinician's order. Using these plus the information encoded on the medication container, the system can (1) verify that the correct medication is given to the correct patient, (2) automatically administer this medication with the correct dosage, frequency, time, and duration, and (3) create a complete record of the medication delivery lifecycle, from clinician order through delivery.

While the it invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed:

1. A method for clinical quality and safety control comprising, by a processing unit:
    receiving and storing, in a database, information relating to one or more of a plurality of patients;
    receiving, a first treatment order from a clinician relative to a first patient, the first treatment order including at least one of the following for treatment of the first patient: a medication or a supply;
    verifying, using the information, an identity of the first patient and accuracy of information included in the first treatment order for treatment of the first patient by the processing unit;
    transmitting, to an order management system associated with a fulfillment center, the first treatment order for the first patient a selection of the fulfillment center being based on information regarding an availability at the fulfillment center of supplies and medications contained in the first treatment order;
    causing the order management system to tag the supplies and medications contained in the first treatment order with an information-carrying facet comprising information relating to the first patient and administration information relating to the supplies and medications contained in the first treatment order based on at least the information contained in the first treatment order;
    causing a robotic mechanism or an autonomous vehicle to transport the supplies and medications contained in the first treatment order with the information-carrying facet to a patient-related location associated with the first patient;
    upon receipt of the supplies and medications contained in the first treatment order with the information-carrying facet at the patient-related location, scanning the information-carrying facet and verifying, by comparing with the first treatment order or the identity of the first patient, scanned information from the information carrying-facet;
    storing, in the database in association with the first patient, a first electronic administration record associated with the first treatment order and making the electronic record accessible through one or more networks, the electronic record including at least an administration schedule of one or more medications included in the first treatment order including dosage and frequency.

2. The method for clinical quality and safety control of claim wherein verifying accuracy of information included in the first treatment order comprises determining whether the supplies and medications contained in the first treatment order are compatible for treating a disease state of the first patient, the disease state identified from information about the first patient stored in the database.

3. The method for clinical quality and safety control of claim further comprising determining, before the transmitting step, whether the clinician is authorized to issue the first treatment order relative to the first patient.

4. The method for clinical quality and safety control of claim 1, wherein the first treatment order is encrypted prior to, during or upon receipt by the order management system.

5. The method of clinical quality and safety control of claim 1, further comprising, upon receipt of the supplies and medications contained in the first treatment order with the information-carrying facet at the patient-related location, verifying whether the supplies contained in the treatment order are compatible with a method of administration based on information included in at least one of the following: the information-carrying facet, identity of the first patient, or the first treatment order.

6. The method of clinical quality and safety control of claim 5, further comprising verifying whether the supplies contained in the treatment order are compatible with a method of administration by determining whether the supplies have one or more of a precision, accuracy, and safeguards to deliver a medication to the first patient at a concentration included in the first treatment order.

7. The method of clinical quality and safety control of claim 1, further comprising, upon receipt of the supplies and medications contained in the first treatment order with the information-carrying facet at the patient-related location, verifying whether the medications contained in the treatment order are compatible with a treatment plan associated with the first patient.

8. The method of clinical quality and safety control of claim 1, further comprising causing a medical device to automatically administer, to the first patient, the one or more medications in accordance with the first electronic administration record.

9. The method of clinical quality and safety control of claim 8, wherein the medical device is an infusion pump.

10. The method for clinical quality and safety control of claim 1, further comprising tagging the first treatment order with environmental data.

11. A system for clinical quality and safety control comprising, the system comprising:
- a robotic mechanism or an autonomous vehicle;
- a memory; and
- a processing unit configured to:
  - receive and store, in a database in the memory, information relating to one or more of a plurality of patients;
  - receive, a first treatment order from a clinician relative to a first patient, the first treatment order including at least one of the following for treatment of the first patient: a medication or a supply;
  - verify, using the information, an identity of the first patient and accuracy of information included in the first treatment order for treatment of the first patient;
  - transmit, to an order management system associated with a fulfillment center, the first treatment order for the first patient, a selection of the fulfillment center being based on information regarding an availability at the fulfillment center of supplies and medications contained in the first treatment order;
  - causing the order management system to tag, based on at least the information contained in the first treatment order, the supplies and medications contained in the first treatment order with an information-carrying facet comprising information relating to the first patient and administration information relating to the supplies and medications contained in the first treatment order;
  - causing the robotic mechanism or the autonomous vehicle to transport the supplies and medications contained in the first treatment order with the information-carrying facet to a patient-related location associated with the first patient;
  - upon receipt of the supplies and medications contained in the first treatment order with the information-carrying facet at the patient-related location, scan the information-carrying facet verify, by comparing with the first treatment order or the identity of the first patient, accuracy of information scanned from the information carrying-facet;
  - store, in the database in association with the first patient, a first electronic administration record associated with the first treatment order and making the electronic record accessible through one or more networks, the electronic record including at least an administration schedule of one or more medications included in the first treatment order including dosage and frequency.

12. The system for clinical quality and safety control of claim 11, wherein the processing unit is configured to verify the accuracy of information included in the first treatment order by determining whether the supplies and medications contained in the first treatment order are compatible for treating a disease state of the first patient, the disease state identified from information about the first patient stored in the database.

13. The system for clinical quality and safety control of claim 11, wherein the processing unit is further configured to determine, before the transmitting step, whether the clinician is authorized to issue the first treatment order relative to the first patient.

14. The system for clinical quality and safety control of claim 11, wherein the processing unit is further configured to tag the first treatment order with environmental data.

15. The system for clinical quality and safety control of claim 11, wherein the processing unit is further configured to encrypt the first treatment order prior to, during or upon receipt by the order management system.

16. The system for clinical quality and safety control of claim 11, wherein the processing unit is further configured to, upon receipt of the supplies and medications contained in the first treatment order with the information-carrying facet at the patient-related location, verify whether the supplies contained in the treatment order are compatible with a method of administration based on information included in at least one of the following: the information-carrying facet, identity of the first patient, or the first treatment order.

17. The system for clinical quality and safety control of claim 16, wherein the processing unit is configured to verify whether the supplies contained in the treatment order are compatible with a method of administration by determining whether the supplies have one or more of a precision, accuracy, and safeguards to deliver a medication to the first patient at a concentration included in the first treatment order.

18. The system for clinical quality and safety control of claim 11, wherein the processing unit is further configured to, upon receipt of the supplies and medications contained in the first treatment order with the information-carrying facet at the patient-related location, verify whether the medications contained in the treatment order are compatible with a treatment plan associated with the first patient.

19. The system for clinical quality and safety control of claim 11, further comprising:
- a medical device configured to administer medication to patients, and
- wherein the processing unit is further configured to cause the medical device to automatically administer, to the first patient, the one or more medications in accordance with the first electronic administration record.

20. The system of clinical quality and safety control of claim 19, wherein the medical device is an infusion pump.

* * * * *